United States Patent [19]

Kanemaru et al.

[11] Patent Number: 5,202,207
[45] Date of Patent: Apr. 13, 1993

[54] ELECTROPHOTOGRAPHIC PHOTOSENSITIVE MEMBER

[75] Inventors: Tetsuro Kanemaru; Shin Nagahara; Akihiro Senoo, all of Tokyo, Japan

[73] Assignee: Canon Kabushiki Kaisha, Tokyo, Japan

[21] Appl. No.: 676,368

[22] Filed: Mar. 28, 1991

[30] Foreign Application Priority Data

Mar. 30, 1990 [JP] Japan .................. 2-80800

[51] Int. Cl.$^5$ .............................. G03G 5/06
[52] U.S. Cl. ........................... 430/59; 430/76; 430/78
[58] Field of Search .......... 430/59, 76, 78, 83, 430/58

[56] References Cited

U.S. PATENT DOCUMENTS

| | | | |
|---|---|---|---|
| 4,150,987 | 4/1979 | Anderson et al. | 96/1.5 R |
| 4,450,218 | 5/1984 | Takei et al. | 430/59 |
| 4,725,518 | 2/1988 | Carmichael et al. | 430/132 |
| 4,777,142 | 10/1988 | Pawlowski | 430/78 |
| 5,049,464 | 9/1991 | Kanemaru et al. | 430/59 |

FOREIGN PATENT DOCUMENTS

| | | |
|---|---|---|
| 0376311 | 7/1990 | European Pat. Off. |
| 2603713 | 3/1988 | France. |
| 61-295558 | 12/1986 | Japan. |
| 62-201447 | 9/1987 | Japan. |
| 2-052360 | 2/1990 | Japan ............ 430/59 |
| 2-306248 | 12/1990 | Japan ............ 430/59 |

*Primary Examiner*—Marion E. McCamish
*Assistant Examiner*—Christopher D. Rodee
*Attorney, Agent, or Firm*—Fitzpatrick, Cella, Harper & Scinto

[57] ABSTRACT

An electrophotographic photosensitive member comprises an electroconductive support and a photosensitive layer formed on the support. The photosensitive layer contains a compound represented by the general formula (I):

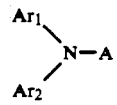

9 Claims, 1 Drawing Sheet

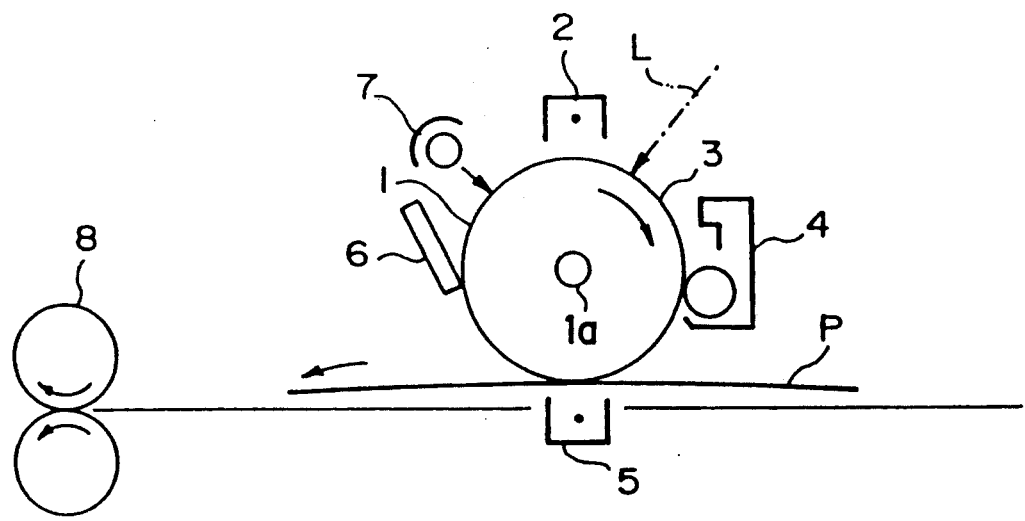
F I G. 1
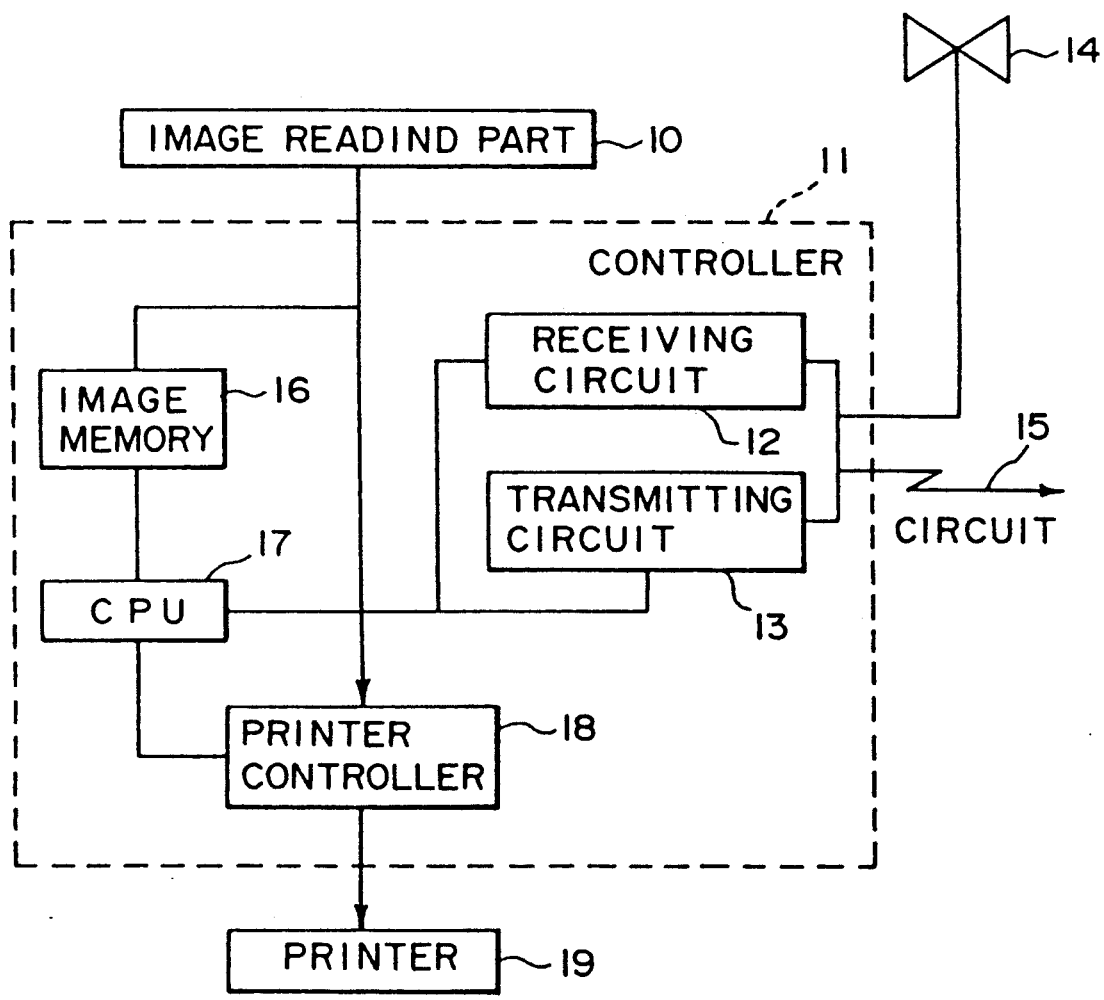
F I G. 2

ELECTROPHOTOGRAPHIC PHOTOSENSITIVE MEMBER

BACKGROUND OF THE INVENTION

1. Field of the Invention

The present invention relates to an electrophotographic photosensitive member having improved electrophotographic characteristics.

2. Related Background Art

In recent year, an electrophotographic photosensitive member of a function-separation type, which comprises separate substances having respectively a charge-generating function and a charge-transporting function, brought about remarkable improvements in sensitivity and durability which had been disadvantages of conventional organic photosensitive members.

Such function-separation type of electrophotographic photosensitive members are advantageous because the substances for the charge-generating material and the charge-transporting material can each be selected from a wide variety of substances, which allows production of an electrophotographic photosensitive member having desired properties relatively easily at low cost.

Various compounds serving charge-transporting function are reported as the charge-transporting substances, including hydrazones as disclosed in U.S. Pat. No. 4,150,987, triazoles and pyrazolines as disclosed in U.S. Pat. No. 3,837,851, stilbenes as disclosed Japanese Patent Laid-Open Application No. 58-198043, benzidines as disclosed in Japanese Patent Laid-Open Application Nos. 61-295558 and 62-201447, and so forth.

One of the characteristics required for charge-transporting substances is resistance to deterioration caused by ozone and NOx produced by corona discharge, and light illumination.

A new problem resulting from recent improvements in durability of photosensitive members and in quality of images is the memory-resting phenomenon. This phenomenon is, in principle, deterioration caused by substances produced by corona discharge, resulting in decrease of chargeability, when the rotation of a sensitive member stops after completion of copying in the vicinity of a corona charger. This leads to decrease of image density in positive development or increase of image density in reversal development at that portion which stops near the corona charger. This phenomenon tends to occur after long time use of the photosensitive member, and is becoming a more and more serious problem with lengthening the life of photosensitive members.

SUMMARY OF THE INVENTION

An object of the present invention is to provide an electrophotographic photosensitive member having excellent electrophotographic characteristics in sensitivity, chargeability, residual potential, etc.

Another object of the present invention is to provide an electrophotographic photosensitive member which has the above excellent electrophotographic characteristics, and yet does not cause memory-resting phenomenon.

According to an aspect of the present invention, there is provided an electrophotographic photosensitive member comprising an electroconductive support and a photosensitive layer formed thereon, the photosensitive layer containing a compound represented by the general formula [I]:

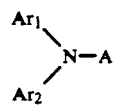

wherein $Ar_1$ and $Ar_2$ are each an aryl group which may be substituted; and A is a group selected from

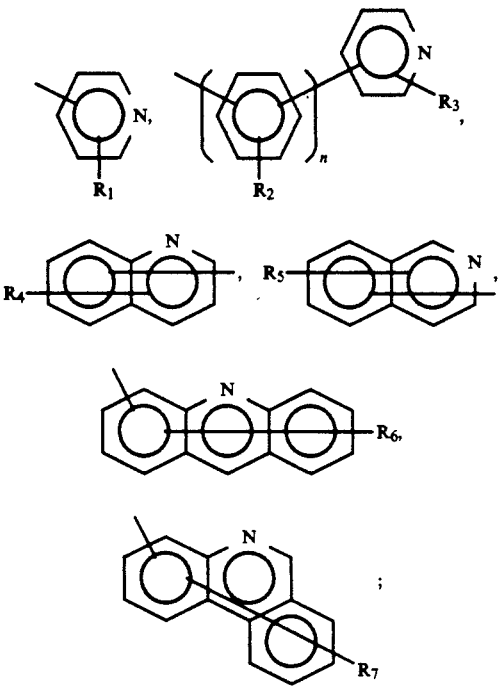

wherein $R_1$, $R_2$, $R_3$, $R_4$, $R_5$, $R_6$, and $R_7$ are each hydrogen, a substituted or unsubstituted alkyl group or a substituted or unsubstituted alkoxy group; and n is an integer of 1 or 2.

According to another aspect of the present invention, there is provided an electrophotographic apparatus, comprising an electrophotographic photosensitive member, a means for forming an electrostatic latent image, a means for developing the electrostatic latent image formed, and a means for transferring an image developed onto a transfer-receiving material: the electrophotographic photosensitive member comprising an electroconductive support and a photosensitive layer formed thereon, and the photosensitive layer containing the compound represented by the above general formula [I].

According to still another aspect of the present invention, there is provided a device unit comprising an electrophotographic photosensitive member, a charging means, and a cleaning means: the electrophotographic photosensitive member comprising an electroconductive support and a photosensitive layer formed thereon, and the photosensitive layer containing the compound represented by the above general formula [I], the device unit supporting the electrophotographic photosensitive member, charging means and the cleaning means in integration, and the device unit being mountable on and demountable from the main body.

According to a further aspect of the present invention, there is provided a facsimile machine, comprising an electrophotography apparatus and a signal-receiving means for receiving image information from a remote terminal: the electrophotography apparatus comprising an electrophotographic photosensitive member, the electrophotographic photosensitive member comprising an electroconductive support and a photosensitive layer formed thereon, and the photosensitive layer containing the compound represented by the above general formula [1].

BRIEF DESCRIPTION OF THE DRAWINGS

FIG. 1 illustrates an outline of constitution of an electrophotographic apparatus employing an electrophotographic photosensitive member of the present invention.

FIG. 2 illustrates an example of a block diagram of a facsimile employing the electrophotographic photosensitive member of the present invention.

DESCRIPTION OF THE PREFERRED EMBODIMENT

The photosensitive layer constituting the electrophotographic photosensitive member of the present invention contains a compound represented by the general formula [I]:

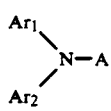

[I]

wherein $Ar_1$ and $Ar_2$ are each an aryl group which may be substituted; A is a group selected from

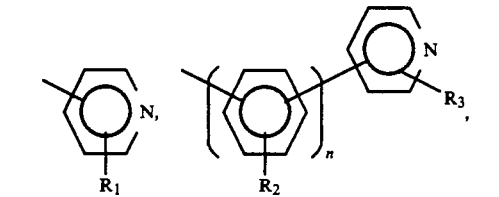

$R_1$, $R_2$, $R_3$, $R_4$, $R_5$, $R_6$, and $R_7$ are each hydrogen, a substituted or unsubstituted alkyl group or a substituted or unsubstituted alkoxy group; and n is an integer of 1 or 2.

In the above formula, the aryl group includes radicals of benzene, naphthalene, anthracene, biphenyl, terphenyl, and the like; the alkyl group includes methyl, ethyl, propyl, and the like; and the alkoxy group includes methoxy, ethoxy and the like. The substitutent thereon includes alkyl groups such as methyl, ethyl, propyl, etc., alkoxy groups such as methoxy, ethoxy, etc., and halogen atoms such as fluorine, chlorine, bromine, etc. A is preferably

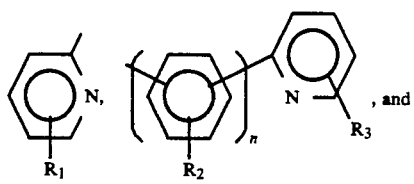

and particularly preferable are

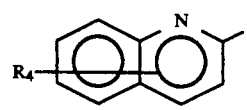

Specific examples of the compounds which are useful in the present invention are shown below without limiting the present invention in any way.

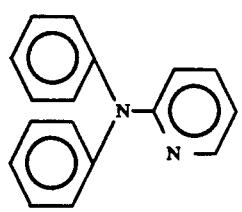

Exemplified compounds (1)

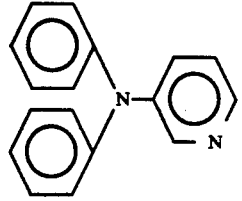

Exemplified compounds (2)

-continued
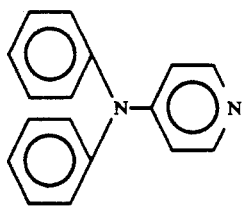
Exemplified compounds (3)
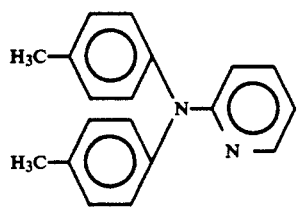
Exemplified compounds (4)
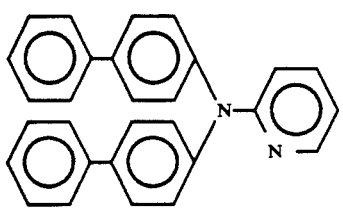
Exemplified compounds (5)
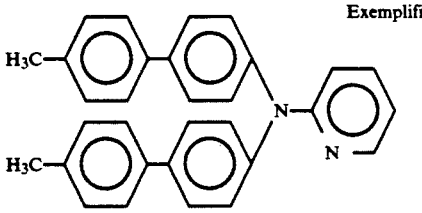
Exemplified compounds (6)
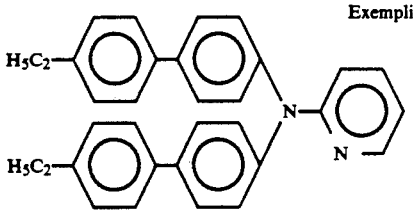
Exemplified compounds (6)
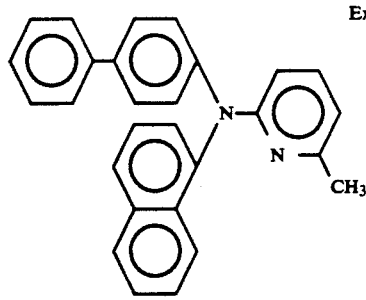
Exemplified compounds (8)
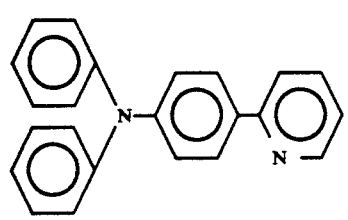
Exemplified compounds (9)
-continued
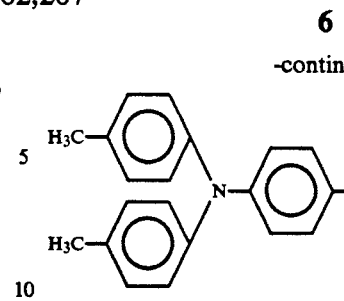
Exemplified compounds (10)
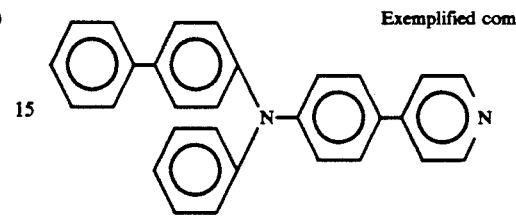
Exemplified compounds (11)
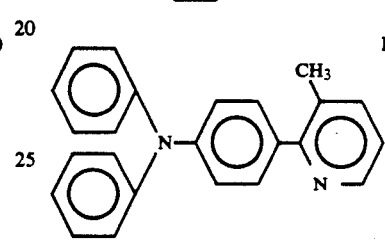
Exemplified compounds (12)
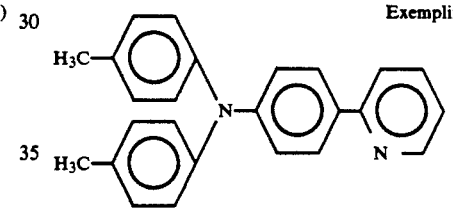
Exemplified compounds (13)
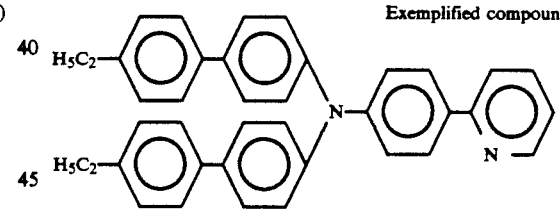
Exemplified compounds (14)
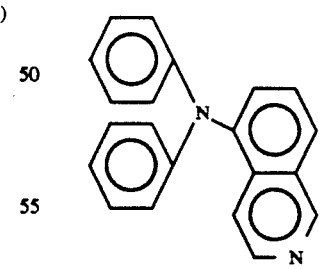
Exemplified compounds (15)
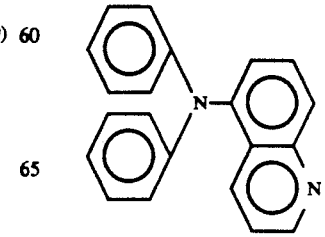
Exemplified compounds (16)

-continued
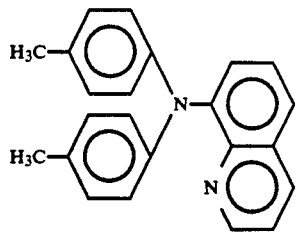
Exemplified compounds (17)
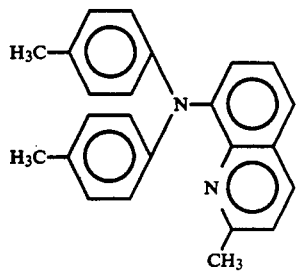
Exemplified compounds (18)
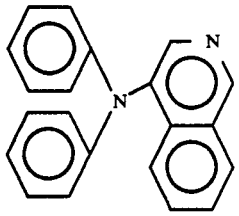
Exemplified compounds (19)
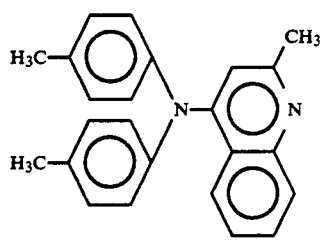
Exemplified compounds (20)
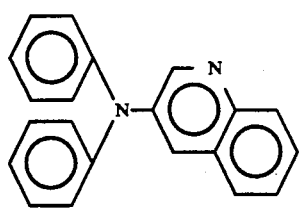
Exemplified compounds (21)
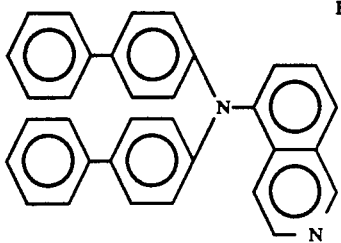
Exemplified compounds (22)
-continued
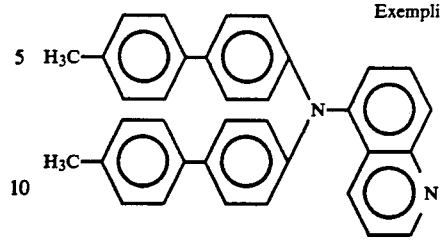
Exemplified compounds (23)
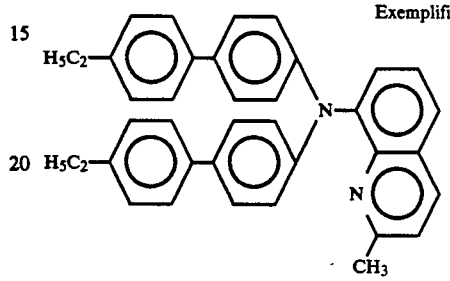
Exemplified compounds (24)
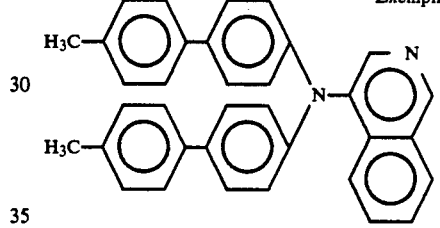
Exemplified compounds (25)
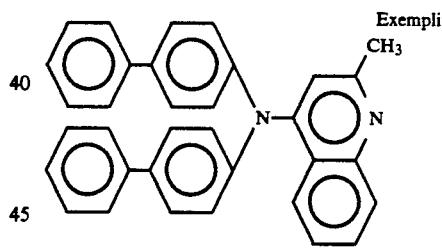
Exemplified compounds (26)
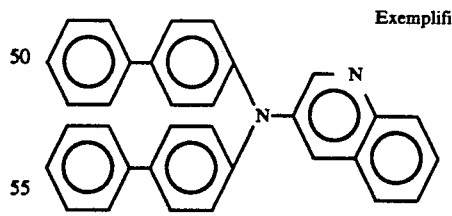
Exemplified compounds (27)
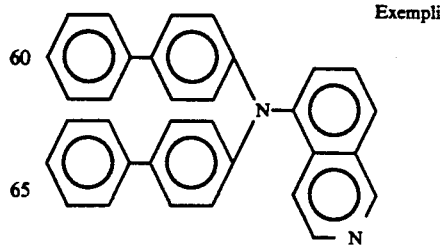
Exemplified compounds (28)

Exemplified compounds (29)

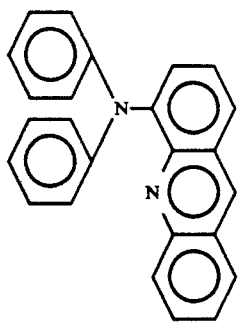

Exemplified compounds (30)

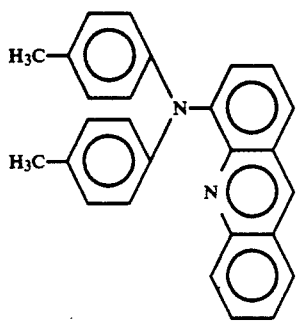

Exemplified compounds (31)

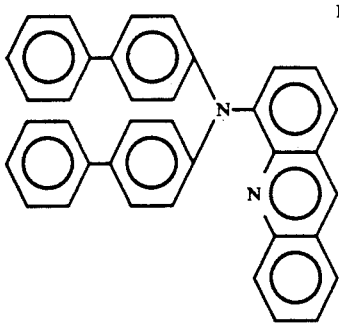

Exemplified compounds (32)

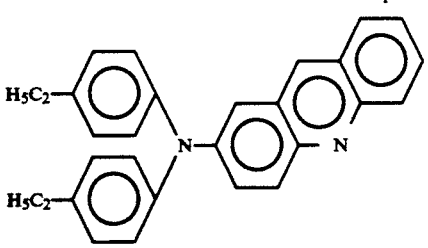

Exemplified compounds (33)

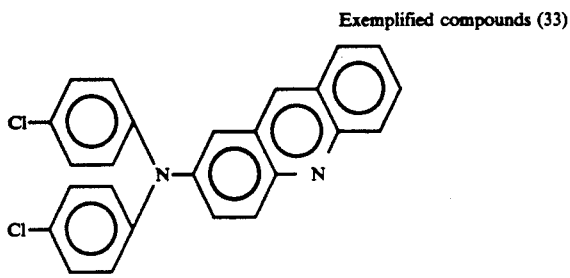

Exemplified compounds (34)

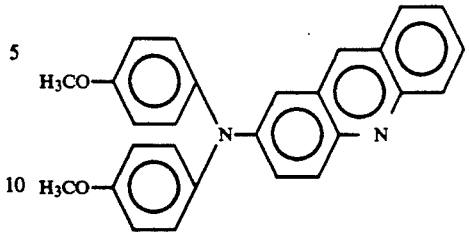

Exemplified compounds (35)

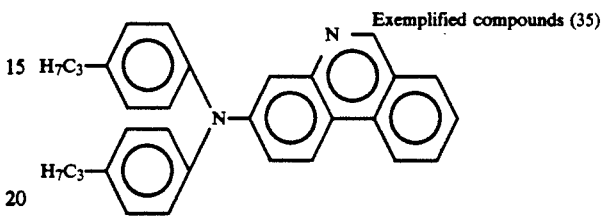

Exemplified compounds (36)

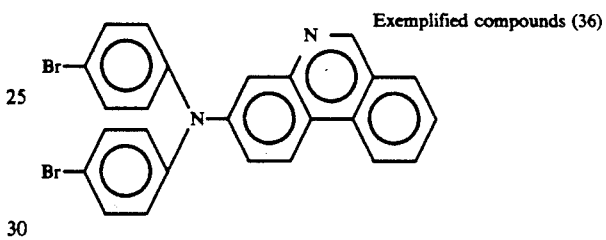

SYNTHESIS EXAMPLE

Synthesis of Exemplified compound (1)

2.0 g (11.75 mmol) of 2-anilinopyridine, 6.49 g (47.00 mmol) of anhydrous potassium carbonate, 9.59 g (47.00 mmol) of iodobenzene, and 2.0 g of powdery copper were placed in a 100-ml three-necked flask, and refluxed under heating by means of a mantle heater for 8 hours to allow reaction to proceed. After the reaction, the content in the flask was filtered, and from the filtrate, iodobenzene was removed off by vacuum distillation. To the distillation residue, methanol was added to deposit a crystalline matter. The crystalline matter was washed with methanol, and separated and purified by employing a silica gel column to obtain the intended compound in an amount of 2.00 g (yield: 69.0%).

Elemental analysis:
Calculated: C, 82.93%; H, 5.69%; N, 11.38%.
Found: C, 82.90%; H, 5.61%; N, 11.49%.

The compounds of the present invention other than Exemplified compound (1) can be synthesized in the same manner as stated above. However, the method of synthesis is not limited thereto.

The electrophotographic photosensitive member of the present invention comprises a photosensitive layer on an electroconductive support. The constitution of the photosensitive layer includes the types as shown below. In the types (1), (2), and (4), the layers are shown in the order of (Lower layer)/(Upper layer).

(1) Layer containing a charge-generating substance/layer containing a charge-transporting substance, (2) Layer containing a charge-transporting substance/layer containing a charge-generating substance, (3) Layer containing a charge-generating substance and a charge-transporting substance, (4) Layer containing a charge-generating substance/layer containing a charge-transporting substance/layer for protection.

The compound represented by the general formula [1] has a high ability for transporting positive holes. In the types (1) and (4) of photosensitive layers, the compound is preferably employed for negative charges; in type (2) the compound is preferably employed for positive charges; and in types (3), the compound may be employed both for positive charges and for negative charges.

The constitution of the electrophotographic photosensitive member of the present invention is, of course, not limited to the above-mentioned fundamental constitution.

The particularly preferable type of the photosensitive layers of the present invention are those of the type (1). Detailed description is given below.

The charge-transporting layer in the present invention is preferably formed by dissolving a compound represented by the general formula [I] and a binder in an appropriate solvent, applying the resulting solution on a support, and drying it.

The compound of the general formula [I] may be used with another charge-transporting substance in combination.

The binder useful for the charge-transporting layer includes polyarylates, polysulfones, polyamides, acrylic resins, acrylonitrile resins, methacrylic resins, vinyl chloride resins, vinyl acetate resins, phenol resins, epoxy resins, polyester resins, alkyd resins, polycarbonates, polyurethanes, and copolymers such as styrene-butadiene copolymers, styrene-acrylonitrile copolymers, and styrene-meleic anhydride copolymers, and the like. Further in addition to such insulative resins, the binder includes organic photoconductive polymers such as polyvinylcarbazole, polyvinylanthracene, and polyvinylpyrene.

The charge-transporting substance in the present invention is mixed with the binder preferably in an amount of from 10 to 500 parts by weight based on 100 parts by weight of the binder.

The charge-transporting layer, which may be laminated either outside or inside the charge-generating layer, has a function of receiving charge carriers from the charge-generating layer and transporting the carriers.

The charge-transporting layer has a film thickness preferably in the range of from 5 μm to 40 μm, more preferably from 10 μm to 30 μm.

The organic solvent used forming the charge-transporting layer is preferably selected from those which dissolve neither the charge-generating layer nor the subbing layer mentioned later, depending on the binder employed. Specifically, the organic solvent includes alcohols such as methanol, ethanol, and isopropanol; ketones such as acetone, methyl ethyl ketone, and cyclohexanone; amides such as N,N-dimethylformamide, and N,N-dimethylacetamide; sulfoxides such as dimethylsulfoxide; ethers such as tetrahydrofuran, dioxane, and ethylene glycol monomethyl ether; esters such as methyl acetate, and ethyl acetate; aliphatic halogenated hydrocarbons such as chloroform, carbon tetrachloride, and trichloroethylene; aromatic solvents such as benzene, toluene, xylene, chlorobenzene, and dichlorobenzene.

The charge-transporting layer in the present invention may contain various additives, including a plasticizer such as diphenyl, m-terphenyl, and dibutyl phthalate; a surface lubricant such as silicone oils, graft-type silicone polymers, and various fluorocarbons; a potential stabilizer such as dicyanovinyl compounds, and carbazole derivatives; an antioxidant such as β-carotene, nickel complexes, and 1,4-diazabicyclo[2.2.2]octane; and the like.

The charge-generating layer in the present invention contains a charge-generating material selected from inorganic charge-generating substances including selenium, selenium-tellurium, amorphous silicon, and the like; and organic charge-generating substances including cationic dyes such as pyrylium dyes, thiapyrylium dyes, azulenium dyes, thiacyanine dyes, and quinocyanine dyes; squarilium salt dyes, phthalocyanine pigments, polycyclic quinone pigments such as anthoanthrone pigments, dibenzopyrene quinone pigments and pyranthorone pigment; indigo pigment, quinacridone pigments, and azo pigments, and the like. The substance may be used singly or in combination of two or more thereof. The layer may be in a form of a vapor deposition layer or a coating layer.

In the charge-generating substances, the azo dyes particularly include a vast variety of compounds. Typical examples of the highly effective azo pigments are shown below.

The general formula of the azo pigments are shown as $$A\text{-}(N{=}N\text{---}Cp)_n$$

wherein A is central skeleton, Cp is a coupler moiety, and n is an integer of 2 or 3.

Specific examples of "A" are as mentioned below:

A-1

(R: H, Cl and —OCH₃)

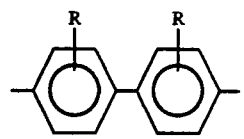

A-2

(R: H and —CN)

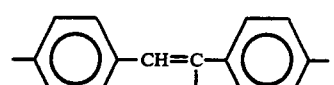

A-3

(R: H and —CN)

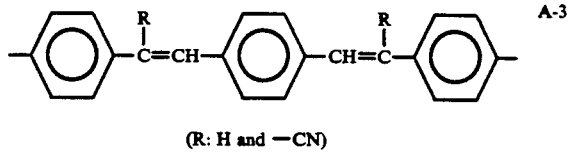

A-4

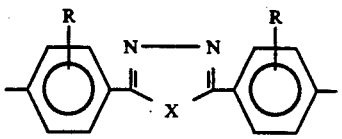

(X: O and S
R: H, —CH₃ and Cl)

-continued
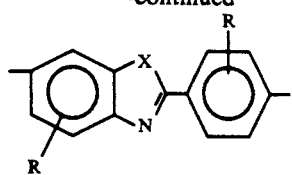
A-5
(X: O and S
R: H, —CH₃ and Cl)
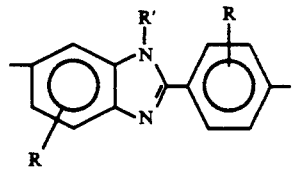
A-6
(R: H, —CH₃, Cl
R': H, —CH₃ and —C₆H₅)
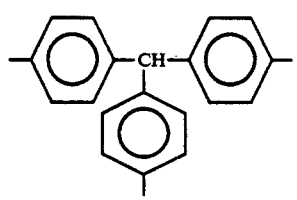
A-7
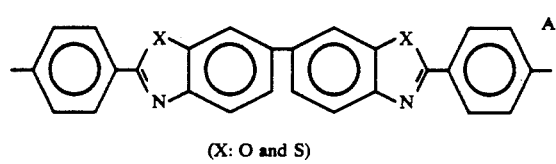
A-8
(X: O and S)
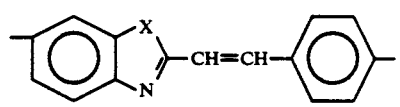
A-9
(X: O and S)
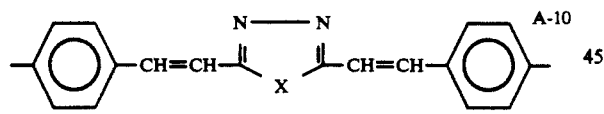
A-10
(X: O and S)
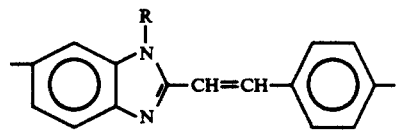
A-11
(R: H and —CH₃)
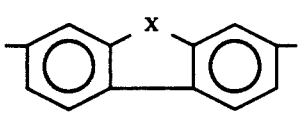
A-12
(X: =CH₂, O, S and =SO₂)
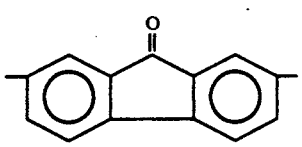
A-13
-continued
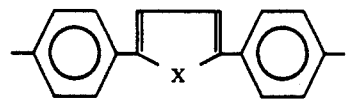
A-14
(X: O and S)
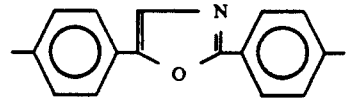
A-15
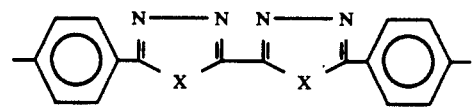
A-16
(X: O and S)
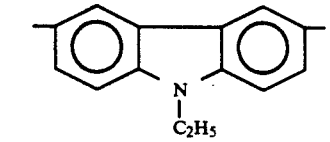
A-17
A-18
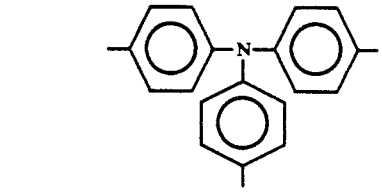
A-19
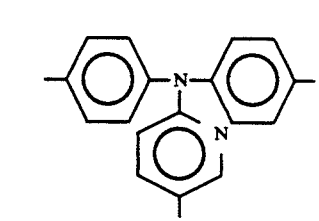
A-20
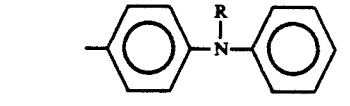
A-21
(R: H and —CH₃)
The specific examples of "Cp" are mentioned below:
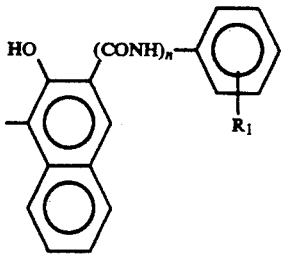
Cp-1

-continued (R: H, halogen, alkoxy, alkyl, nitro, etc.)

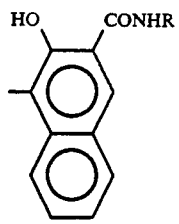

(R: —CH$_3$, —C$_2$H$_5$, and —C$_3$H$_7$)

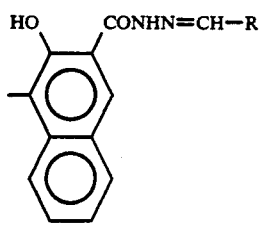

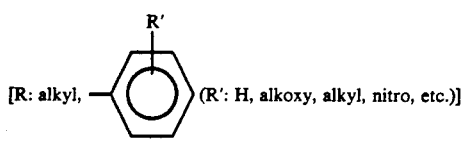

[R: alkyl, (R': H, alkoxy, alkyl, nitro, etc.)]

Cp-4

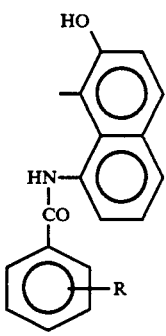

(R: H, halogen, alkoxy, alkyl, nitro, etc.)

Cp-5

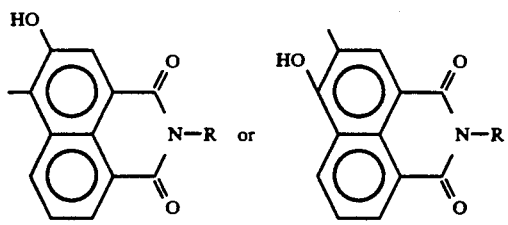

Cp-6

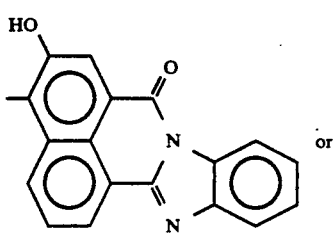

Cp-2

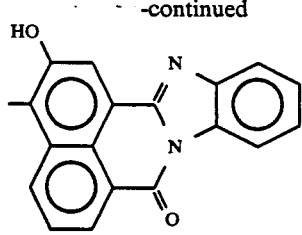

Cp-3

Cp-7

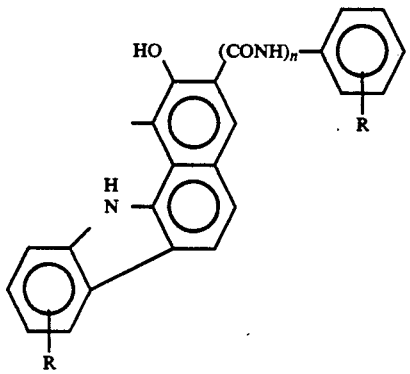

(R: H, halogen, alkyl, nitro, etc., n: 1 or 2)

These central skeletons A and these couplers Cp are suitably combined to form the charge-generating substance.

Phthalocyanine pigments having no metal or having a central metal are also suitable for the charge-generating substance.

The charge-generating layer can be formed by dispersing the above-mentioned charge-generating substance in a suitable binder and applying the resulting dispersion on a support. It can also be formed as a vapor deposition film by means of a vacuum vapor deposition apparatus.

The binder is selected from a wide variety of insulative resins and organic photoconductive polymers such as poly-N-vinylcarbazole and polyvinylpyrene.

The resins preferable as the binder include insulative resins such as polyvinylbutyral, polyarylate (a polycondensate of bisphenol A with phthalic acid, and the like), polycarbonates, polyesters, polyvinyl acetate, acrylic resins, polyacrylamides, polyamides, cellulose resins, urethane resins, epoxy resins, polyvinyl alcohols, and the like.

The resin is contained in the charge-generating layer preferably in an amount of not more than 80% by weight, more preferably not more than 40% by weight.

The organic solvent employed in the coating process includes alcohols, ketones, amides, sulfoxides, ethers, esters, aliphatic halogenated hydrocarbons, aromatic solvents and the like.

The thickness of the charge-generating layer is preferably not more than 5 μm, more preferably in the range of from 0.01 to 1 μm.

The charge-generating layer may further contain a sensitizing agent.

Between the electroconductive support and the photosensitive layer, another layer having both a barrier function and an adhesion function, namely a subbing layer, may be provided in the present invention.

The material for the subbing layer includes polyvinyl alcohol, polyethylene oxide, ethylcellulose, methylcellulose, casein, polyamides, glue, gelatin, and the like.

The subbing layer can be formed by dissolving the above material in an appropriate solvent and applying the resulting solution on an electroconductive support. The thickness of the layer is preferably not more than 5 μm, more preferably in the range of from 0.2 μm to 3.0 μm.

Further, for protecting the photosensitive layer from various external mechanical and electrical forces, a simple resin layer or a resin layer containing a compound of the present invention and/or an electroconductive substance dispersed therein may be provided on the photosensitive layer as a protective layer.

In the case where a protective layer is provided as above, the photosensitive layer including the protective layer is simply referred to as a "photosensitive layer".

The layers mentioned above can be formed on an electroconductive support by coating such as immersion coating, spray coating, spinner coating, roller coating, Meyer-bar coating, and blade coating by use of a suitable organic solvent.

The electroconductive support includes the supports which are made of a metal or a metal alloy and are electroconductive by themselves such as aluminum, aluminum alloys, and stainless steel; plastic sheets having electroconductive coating layer made by vapor deposition of aluminum, an aluminum alloy, indium oxide, tin oxide or the like; supports made of a plastic, a metal or a metal alloy having a layer thereon made by applying electroconductive particles together with a suitable binder; supports made of plastic or paper impregnated with electroconductive particles; plastics containing an electroconductive polymer; and the like.

The electrophotographic photosensitive member of the present invention is not only useful for electrophotographic copying machines but also useful for a variety of application fields of electrophotography such as laser printers, CRT printers, electrophotographic engraving systems, and the like.

FIG. 1 shows a schematic diagram of a conventional transfer type electrophotographic apparatus employing the electrophotographic photosensitive member of the present invention.

In FIG. 1, a drum type photosensitive member 1 serves as an image carrier, being driven to rotate around the axis 1a in the arrow direction at a predetermined peripheral speed. The photosensitive member 1 is charged positively or negatively at the peripheral face uniformly during the rotation by an electrostatic charging means 2, and then exposed to image-exposure light L (e.g. slit exposure, laser beam-scanning exposure, etc.) at the exposure portion 3 with an image-exposure means (not shown in the figure), whereby electrostatic latent images are sequentially formed on the peripheral surface in accordance with the exposed image.

The electrostatic latent image is developed with a toner by a developing means 4, and the toner-developed images are sequentially transferred by a transfer means 5 onto a transfer-receiving material P which is fed between the photosensitive member 1 and the transfer means 5 synchronously with the rotation of the photosensitive member 1 from a transfer-receiving material feeder not shown in the figure.

The transfer-receiving material P having received the transferred image is separated from the photosensitive member surface, and introduced to an image fixing means 8 for fixation of the image and discharged from the copying machine as a duplicate copy.

The surface of the photosensitive member 1, after the image transfer, is cleaned with a cleaning means 6 to remove any remaining non-transferred toner, and is treated with a pre-exposing means 7 to eliminate for electrostatic charge and repeatedly used for image formation.

The generally and usually employed charging means 2 for uniformly charging the photosensitive member 1 are corona charging apparatuses. The generally and usually employed transfer means 5 are also a corona charging means. In the electrophotographic apparatus, two or more of the constitutional elements of the above described photosensitive member, the developing means, the cleaning means, etc. may be integrated as one apparatus unit, which may be made demountable from the main body of the apparatus. For example, at least one an electrostatic charging means, a developing means, and a cleaning means is combined with the photosensitive member into one unit demountable from the main body of the apparatus by aid of a guiding means such as a rail provided on the main body of the apparatus. An electrostatic charging means and/or a developing means may be combined with the aforementioned unit.

In the case where the electrophotographic apparatus is used as a copying machine or a printer, the optical image exposure light L is projected onto a photosensitive member as reflected light or transmitted light from an original copy, or otherwise projected by converting to a signal the information read out with a sensor from an original copy and then according to the signal, scanning with a laser beam, driving an LED array, or driving a liquid crystal shutter array onto a photosensitive member.

In the case where the electrophotographic apparatus is used as a printer of a facsimile apparatus, the optical image exposure light L is for printing the received data. FIG. 2 is a block diagram of an example of this case.

A controller 11 controls an image reading part 10 and a printer 19. The whole of the controller 11 is controlled by a CPU 17. Readout data from the image reading part is transmitted through a transmitting circuit 13 to the other communication station. Data received from the other communication station is transmitted through a receiving circuit 12 to a printer 19. The image data is stored in image memory. A printer controller 18 controls a printer 19. The numeral 14 denotes a telephone set.

The image received through a circuit 15, namely image information from a remote terminal connected through the circuit, is demodulated by the receiving circuit 12, treated for decoding of the image information in CPU 17, and successively stored in the image memory 16. When at least one page of images is stored in the image memory 16, the image is recorded in such a manner that the CPU 17 read out the one page of image information, and send out the one page of decoded information to the printer controller 18, which controls the printer 19 on receiving the one page of information from CPU 17 to record the image information.

Incidentally the CPU 17 receives the following page of information while recording is conducted by the printer 19.

Images are received and recorded in the manner as described above.

EXAMPLE 1

An aluminum cylinder of 80 mm in diameter, and 360 mm in length was employed as the electroconductive support. On this support, 5% solution of a polyamide (trade name: Amylan CM-8000, made by Toray Industries, Inc.) in methanol was applied by immersion to form a subbing layer of 0.5 μm thick.

10 parts of the trisazo pigment of the structural formula below as the charge-generating substance (hereinafter the term "part" being based on weight):

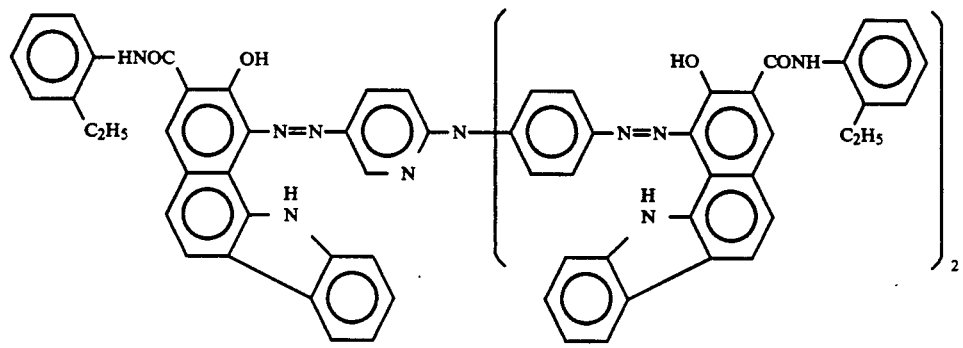

and 7 parts of polyvinylbutyral (trade name: S-LEC BL-S, made by Sekisui Chemical Co., Ltd.) were dispersed in 60 parts of cyclohexanone by a sand mill employing glass beads. To the resulting dispersion, 100 parts of methyl ethyl ketone was added, and the mixture was applied on the above subbing layer to form a charge-generating layer of 0.22 μm thick.

10 parts of the Exemplified compound (9) as the charge-transporting substance and 12 parts of a polycarbonate (trade name: Panlite L-1250, made by Teijin Kasei K. K.) were dissolved in a mixture of 50 parts of dichloromethane and 10 parts of chlorobenzene. The resulting solution was applied on the above-mentioned charge-generating layer to form a charge-transporting layer of 18 μm thick. Thereby an electrophotographic photosensitive member was prepared.

This photosensitive member was mounted on a modified copying machine NP-3525 made by Canon K. K. By use of this copying machine, the properties were evaluated as below.

The latent image forming conditions were set to give the dark portion potential ($V_D$) and the light portion potential ($V_L$) of −650 V and −150 V, respectively, and the quantity of the image exposure was measured as the initial sensitivity.

After successive copying for 5000 sheets, the potentials were measured, and the change rates of $V_D$ and $V_L$ were obtained. For example, "change rate 2% of $V_D$" means that the $V_D$ changed by 2% of 650 V, namely by 13 V.

Thereafter, the photosensitive member was left standing in the copying machine for 10 hours, and the surface potentials were measured.

The portion of the photosensitive member which was kept under the corona charger during the 10-hour standing was marked, and the difference of $V_D$ between that portion and the other portion ($\Delta V_D$) was measured. Further, 5000 sheets successive copying was conducted (10,000 sheets in total), and the same measurements as stated above were made again. After the second 5000-sheet copying, the same portion of the photosensitive member positioned under the corona charger was made to be the same as in the first 500-sheet copying test.

The test results were shown in Table 1.

EXAMPLES 2-5

Electrophotographic photosensitive members were prepared and evaluated in the same manner as in Example 1 except that, as the charge-transporting substances, Exemplified compounds (12), (13), (14), and (24) were each used in place of Exemplified compound (9) used in Example 1.

The test results were shown in Table 1.

COMPARATIVE EXAMPLES 1-5

Electrophotographic photosensitive members were prepared and evaluated in the same manner as in Example 1 except that Exemplified comparative compounds (1), (2), (3), (4), and (5) of the structural formulas shown below were each used in place of Exemplified compound (9) used in Example 1.

Comparative exemplified compound (1)

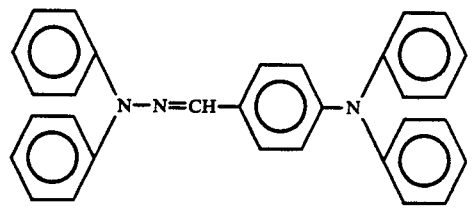

Comparative exemplified compound (2)

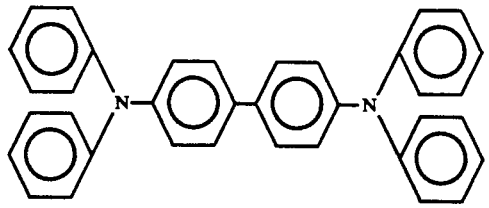

Comparative exemplified compound (3)

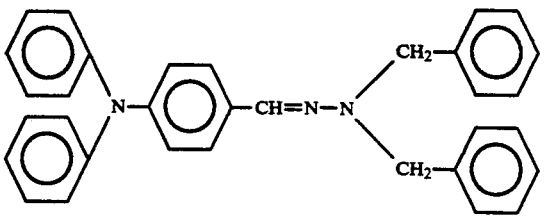

Comparative exemplified compound (4)

-continued

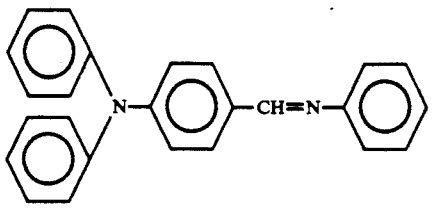

Comparative exemplified compound (5)

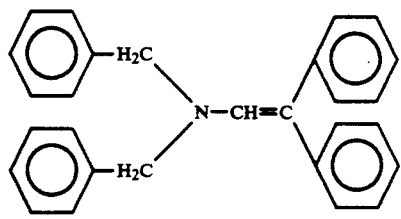

The test results are shown in Table 1.

50 parts of cyclohexanone by a sand mill employing glass beads. To the resulting dispersion, 100 parts of methyl ethyl ketone was added, and the mixture was applied on the above subbing layer to form a charge-generating layer of 0.15 μm thick.

100 parts of the compound represented by the formula shown below:

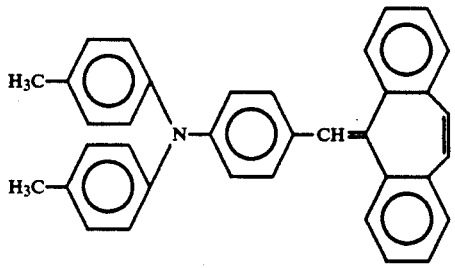

and 2 parts of the Exemplified compound (9) as the charge-transporting substances, and 100 parts of a polycarbonate (trade name: Panlite L-1250, made by Teijin

TABLE 1

| Exemplified Compound Comparative Exemplified Compound | | Initial Sensitivity (lux · sec) | $V_D$ Change Rate (%) 5,000/10,000 sheets | | $V_L$ Change Rate (%) 5,000/10,000 sheets | | $\Delta V_D$ (V) after standing 5,000/10,000 sheets | |
|---|---|---|---|---|---|---|---|---|
| Example | | | | | | | | |
| 1 | (9) | 2.1 | 2.0 | 2.9 | 1.1 | 1.8 | 5 | 7 |
| 2 | (12) | 2.0 | 3.1 | 3.8 | 2.1 | 3.1 | 10 | 12 |
| 3 | (13) | 1.8 | 2.5 | 3.0 | 4.2 | 4.7 | 7 | 8 |
| 4 | (14) | 1.9 | 1.8 | 3.0 | 3.5 | 3.9 | 11 | 13 |
| 5 | (24) | 2.5 | 2.2 | 2.7 | 2.8 | 2.9 | 4 | 14 |
| Comparative Example | | | | | | | | |
| 1 | (1) | 3.7 | 15.0 | 18.4 | 15.1 | 15.7 | 20 | 35 |
| 2 | (2) | 2.9 | 12.0 | 13.5 | 20.6 | 27.4 | 45 | 70 |
| 3 | (3) | 9.0 | 14.9 | 17.4 | 19.3 | 29.0 | 41 | 49 |
| 4 | (4) | 4.2 | 20.1 | 29.2 | 30.4 | 35.4 | 50 | 75 |
| 5 | (5) | 7.8 | 20.0 | 24.5 | 15.9 | 19.9 | 29 | 35 |

EXAMPLE 6

An aluminum cylinder 80 mm in diameter, and 360 mm in length was employed as the electroconductive support. On this support, 5% solution of a polyamide (trade name: Amylan CM-8000, made by Toray Industries, Inc.) in methanol was applied by immersion to form a subbing layer of 0.7 μm thick.

10 parts of the disazo pigment of the structural formula shown below as the charge-generating substance (hereinafter the term "parts" being based on weight):

Kasei K. K.) were dissolved in a mixture of 500 parts of dichloromethane and 100 parts of chlorobenzene. The solution was applied on the above-mentioned charge-generating layer to form a charge-transporting layer 21 μm thick. Thereby an electrophotographic photosensitive member was prepared.

The electrophotographic characteristics of this electrophotographic photosensitive member was evaluated in the same manner as in Example 1. The results are shown in Table 2.

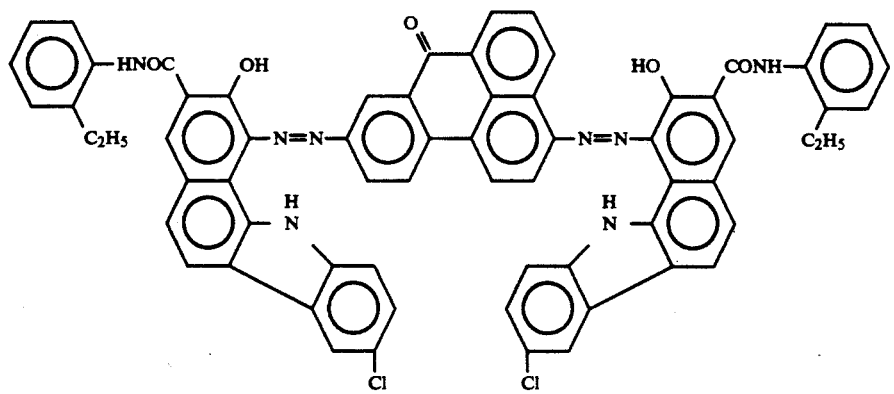

5 parts of polyvinylbutyral (trade name: S-LEC BL-S, made by Sekisui Chemical Co., Ltd.), were dispersed in

EXAMPLES 7-10

Electrophotographic photosensitive members were prepared and evaluated in the same manner as in Example 6 except that, as the charge-transporting substances, Exemplified compounds (12), (13), (14), and (24) were each used in place of Exemplified compound (9) used in Example 6.

The test results were shown in Table 2.

COMPARATIVE EXAMPLE 6

An electrophotographic photosensitive member was prepared and evaluated in the same manner as in Example 6 except that the Exemplified compound (9) used in Example 6 was not added to the charge-transporting layer.

The results are shown in Table 2.

form a charge-generating layer having a dry film thickness of 0.37 μm.

10 parts of Exemplified compound (13) as a charge-transporting substance, 9 parts of poly(4,4-isopropylidenediphenylene carbonate) were dissolved in a mixture of 50 parts of dichloromethane and 10 parts of chlorobenzene to prepare coating liquid for a charge-transporting layer. This coating liquid was applied on the above-mentioned charge-generating layer with a Meyer bar to gice a dry thickness of 17 μm. Thereby an electrophotographic photosensitive member was prepared.

This photosensitive member was evaluated for electrophotographic characteristics in the same manner as in Example 1.

The results are shown in Table 3.

TABLE 2

| Exemplified Compound Comparative Exemplified Compound | | Initial Sensitivity (lux · sec) | $V_D$ Change Rate (%) 5,000/10,000 sheets | | $V_L$ Change Rate (%) 5,000/10,000 sheets | | $\Delta V_D$ (V) after standing 5,000/10,000 sheets | |
| --- | --- | --- | --- | --- | --- | --- | --- | --- |
| Example | | | | | | | | |
| 6 | (9) | 1.7 | 1.1 | 1.9 | 2.5 | 3.0 | 3 | 5 |
| 7 | (12) | 1.8 | 1.9 | 2.7 | 1.8 | 2.7 | 10 | 11 |
| 8 | (13) | 1.7 | 2.7 | 3.9 | 3.0 | 4.1 | 10 | 20 |
| 9 | (14) | 1.7 | 2.6 | 3.5 | 1.9 | 4.0 | 7 | 8 |
| 10 | (24) | 1.8 | 2.0 | 2.2 | 2.1 | 2.9 | 9 | 12 |
| Comparative Example 6 | — | 1.8 | 4.5 | 7.1 | 5.9 | 9.1 | 70 | 120 |

EXAMPLE 11

3 parts of 4-(dimethylaminophenyl)-2,6-diphenylthiapyrylium perchlorate and 3 parts of poly(4,4'-isopropylidenediphenylene carbonate) were dissolved completely in 200 ml of dichloromethane. Thereto, 1000 ml of toluene was added to precipitate an eutectic complex. The precipitate was collected by filtration and, re-dissolved in dichloromethane. To the solution, 100 ml of n-hexane was added to give a precipitate of the eutectic complex.

6 g of this eutectic complex was added to 95 ml of a methanol solution containing 2.5 g of polyvinylbutyral. The mixture was dispersed by means of a ball mill for 10 hours. The liquid dispersion was applied on a casein-layer-coated aluminum plate by use of a Meyer bar to

COMPARATIVE EXAMPLE 7

An electrophotographic photosensitive member was prepared and evaluated in the same manner as in Example 11 except that Exemplified comparative compound (1) was used in place of Exemplified compound (13) used in Example 11.

The results are shown in Table 3.

TABLE 3

| Exemplified Compound Comparative Exemplified Compound | | Initial Sensitivity (lux · sec) | $V_D$ Change Rate (%) 5,000/10,000 sheets | | $V_L$ Change Rate (%) 5,000/10,000 sheets | | $\Delta V_D$ (V) after standing 5,000/10,000 sheets | |
| --- | --- | --- | --- | --- | --- | --- | --- | --- |
| Example 11 | (13) | 3.9 | 7.0 | 8.7 | 2.1 | 4.9 | 5 | 10 |
| Comparative Example 7 | (1) | 5.1 | 15.1 | 19.2 | 10.5 | 16.3 | 45 | 71 |

EXAMPLE 12

Onto an aluminum plate, a 5% solution of a soluble nylon (6-66-610-12 four-component nylon copolymer) in methanol was applied to form a subbing layer of 0.8 μm in dry thickness.

5 g of disazo pigment represented by the structural formula shown below as the charge-generating substance:

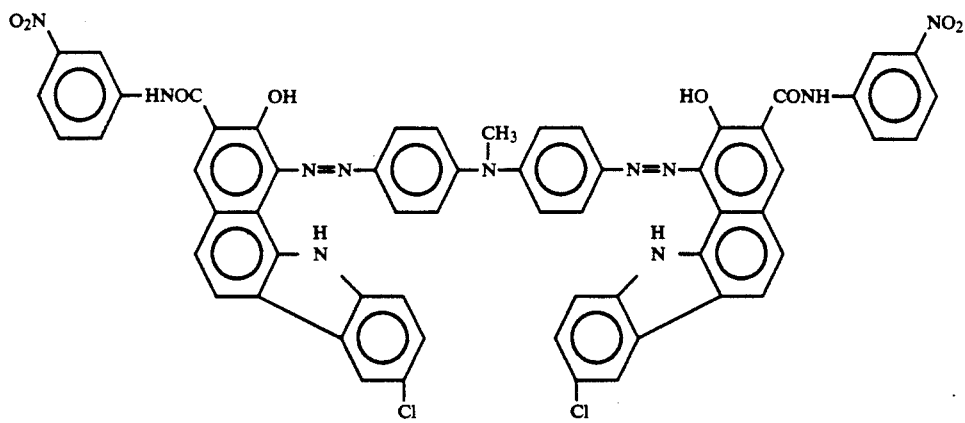

was dispersed in 95 ml of tetrahydrofuran by means of a sand mill for 18 hours.

To this liquid dispersion, a solution of 5 g of Exemplified compound (17) and 10 g of a Z type polycarbonate (viscosity-average molecular weight: 30,000) in 30 ml of chlorobenzene was added, and the mixture was dispersed further for 4 hours by means of a sand mill. The liquid dispersion was applied on the subbing layer formed above with a Meyer bar to form a single layer type photosensitive layer of 20 μm in dry thickness.

The photosensitive member prepared thus was evaluated for electrophotographic characteristics in the same manner as in Example 1 except that the charging polarity was made positive.

The results are shown in Table 4.

COMPARATIVE EXAMPLE 8

An electrophotographic photosensitive member was prepared in the same manner as in Example 12 except that Exemplified comparative compound (2) was used in place of the Exemplified compound (17) used in Example 12. The results are shown in Table 4.

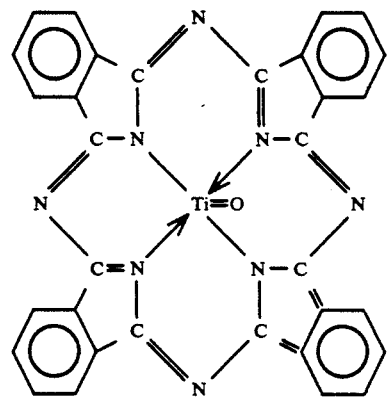

and 6 parts of polyvinylbutyral (trade name: S-LEC BL-S, made by Sekisui Chemical Co., Ltd.) were dispersed in 50 parts of cyclohexanone by a sand mill employing glass beads. To the resulting liquid dispersion,

TABLE 4

| Exemplified Compound Comparative Exemplified Compound | | Initial Sensitivity (lux · sec) | $V_D$ Change Rate (%) 5,000/10,000 sheets | | $V_L$ Change Rate (%) 5,000/10,000 sheets | | $\Delta V_D$ (V) after standing 5,000/10,000 sheets | |
|---|---|---|---|---|---|---|---|---|
| Example 12 | (17) | 4.2 | 5.1 | 6.7 | 4.4 | 4.6 | 4 | 9 |
| Comparative Example 8 | (2) | 7.4 | 17.2 | 18.8 | 7.8 | 10.5 | 25 | 71 |

100 parts of methyl ethyl ketone was added, and the mixture was applied on the above subbing layer to form a charge-generating layer of 0.15 μm thick.

10 parts of the compound of the structural formula shown below as the charge-transporting substance:

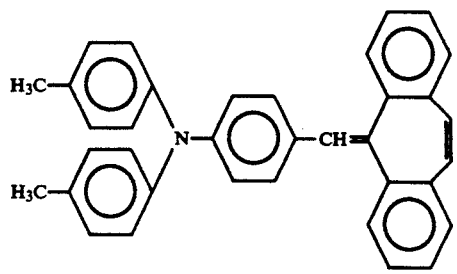

EXAMPLE 13

Onto an aluminum plate, a 5% solution of a soluble nylon (6-66-610-12 four-component nylon copolymer) in methanol was applied to form a subbing layer of 0.8 μm in dry thickness.

10 parts of the compound of the structural formula shown below as the charge-generating substance:

and 10 parts of a polycarbonate (trade name: Panlite L-1250, made by Teijin Kasei K. K.) were dissolved in a mixture of 50 parts of dichloromethane and 10 parts of chlorobenzene. The solution was applied on the above-mentioned charge-generating layer to form a charge-transporting layer of 18 μm thick.

10 parts of the polycarbonate (the same as above), 10 parts of tin oxide, and 0.2 part of Exemplified compound (24) were dispersed in 100 parts of a mixture of cyclohexanone and tetrahydrofuran (1/1). This liquid dispersion was applied on the charge-transporting layer prepared above to form a protective layer of 3 μm thick. Thus an electrophotographic photosensitive member was prepared. This photosensitive member was evaluated for the electrophotographic characteristics in the same manner as in Example 1.

The results are shown in Table 5.

COMPARATIVE EXAMPLE 9

An electrophotographic photosensitive member was prepared and evaluated in the same manner as in Example 13 except that the Exemplified compound (24) used in Example 13 was not added to the protective layer.

The results are shown in Table 5.

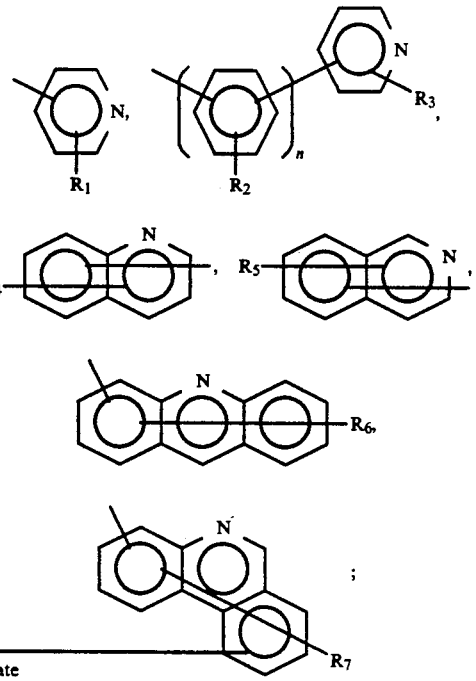

TABLE 5

| Exemplified Compound Comparative Exemplified Compound | | Initial Sensitivity (lux · sec) | $V_D$ Change Rate (%) 5,000/10,000 sheets | | $V_L$ Change Rate (%) 5,000/10,000 sheets | | $\Delta V_D$ (V) after standing 5,000/10,000 sheets | |
|---|---|---|---|---|---|---|---|---|
| Example 13 | (24) | 1.8 | 4.4 | 4.9 | 2.5 | 3.0 | 7 | 15 |
| Comparative Example 9 | — | 2.1 | 15.2 | 16.1 | 9.8 | 15.4 | 61 | 99 |

What is claimed is:

1. An electrophotographic photosensitive member comprising an electroconductive support and a photosensitive layer formed thereon, the photosensitive layer containing a compound represented by the general formula [I] below:

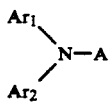

where $Ar_1$ and $Ar_2$ are each an aryl group which may be substituted; and A is a group selected from where $R_1$, $R_2$, $R_3$, $R_4$, $R_5$, $R_6$, and $R_7$ are each hydrogen, a substituted or unsubstituted alkyl group or a substituted or unsubstituted alkoxy group; and n is an integer of 1 or 2.

2. An electrophotographic photosensitive member according to claim 1, wherein the group A is selected from

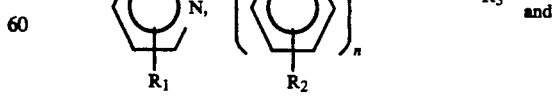

3. An electrophotographic photosensitive member according to claim 2, wherein the group A is selected from

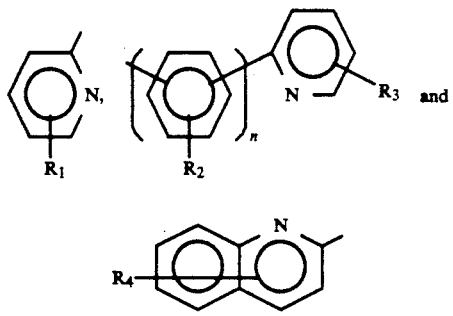

4. An electrophotographic photosensitive member according to claim 1, wherein the photosensitive layer comprises a charge-generating layer and a charge-transporting layer.

5. An electrophotographic photosensitive member according to claim 4, wherein the charge-transporting layer is overlaid on the charge-generating layer.

6. An electrophotographic photosensitive member according to claim 4, wherein the charge-generating layer is overlaid on the charge-transporting layer.

7. An electrophotographic photosensitive member according to claim 1, wherein the photosensitive layer is a single layer.

8. An electrophotographic photosensitive member according to claim 1, wherein a subbing layer is provided between the electroconductive support and the photosensitive layer.

9. An electrophotographic photosensitive member according to claim 1, wherein a protective layer is provided on the photosensitive layer.

* * * * *